(12) United States Patent
Moretti et al.

(10) Patent No.: US 10,548,626 B2
(45) Date of Patent: Feb. 4, 2020

(54) ENDOSCOPIC TISSUE MANIPULATION TOOL

(71) Applicant: Boston Scientific Scimed, Inc., Maple Grove, MN (US)

(72) Inventors: Briana Jean Moretti, Smithfield, RI (US); Matthew Robert Jagelski, West Roxbury, MA (US); John B. Golden, Norton, MA (US); Melissa Joan Horton, Watertown, MA (US); Jennifer Kenyon Saunders, Westport, MA (US); Erin Zinkus, Spencer, MA (US); Gary Paul Pirani, Holden, MA (US); Ellen Asako Kaplan, Irvine, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 535 days.

(21) Appl. No.: 15/377,271

(22) Filed: Dec. 13, 2016

(65) Prior Publication Data
US 2017/0164971 A1  Jun. 15, 2017

Related U.S. Application Data

(60) Provisional application No. 62/267,763, filed on Dec. 15, 2015.

(51) Int. Cl.
*A61B 17/32* (2006.01)
*A61B 17/3205* (2006.01)
(Continued)

(52) U.S. Cl.
CPC .. *A61B 17/32056* (2013.01); *A61B 17/22031* (2013.01); *A61M 5/158* (2013.01);
(Continued)

(58) Field of Classification Search
CPC .......... A61B 17/0218; A61B 17/22031; A61B 17/221; A61B 17/320016; A61B 17/32056; A61B 17/3478; A61B 18/082; A61B 18/1492; A61B 1/00087; A61B 1/00101; A61B 2017/00269; A61B 2017/2215;
(Continued)

(56) References Cited

U.S. PATENT DOCUMENTS 5,290,284 A * 3/1994 Adair ................. A61B 17/0467
606/37
5,938,668 A * 8/1999 Scirica ............... A61B 17/0469
606/139
(Continued)

*Primary Examiner* — Michael F Peffley
*Assistant Examiner* — Amanda L Zink
(74) *Attorney, Agent, or Firm* — Bookoff McAndrews, PLLC

(57) ABSTRACT

A medical device configured to manipulate tissue within a body of a subject may include an elongate shaft having a proximal end and a distal end. The distal end of the shaft may be configured to be inserted into the body. The device may include end effectors coupled to the distal end of the elongate shaft. The end effectors may include a needle pivotably coupled to the shaft and configured to inject a fluid into the tissue. The end effectors may also include an articulating arm pivotably coupled to the shaft, and a cutting wire extending between the needle and the arm.

20 Claims, 4 Drawing Sheets

(51) Int. Cl.
  *A61B 17/22* (2006.01)
  *A61M 5/158* (2006.01)
  *A61B 17/00* (2006.01)
  *A61B 18/00* (2006.01)
  *A61B 18/14* (2006.01)

(52) U.S. Cl.
  CPC ........... *A61B 17/320016* (2013.01); *A61B 2017/00269* (2013.01); *A61B 2018/00494* (2013.01); *A61B 2018/00601* (2013.01); *A61B 2018/144* (2013.01)

(58) Field of Classification Search
  CPC .... A61B 17/32006; A61B 2018/00029; A61B 2018/00494; A61B 2018/00595; A61B 2018/00601; A61B 2018/144; A61M 5/158
  See application file for complete search history.

(56) References Cited

U.S. PATENT DOCUMENTS

| | | | |
|---|---|---|---|
| 6,267,759 B1 * | 7/2001 | Quick | A61B 17/32002 204/620 |
| 6,352,503 B1 * | 3/2002 | Matsui | A61B 1/00071 600/104 |
| 6,355,030 B1 * | 3/2002 | Aldrich | A61B 18/08 606/28 |
| 6,736,828 B1 * | 5/2004 | Adams | A61B 17/00234 606/151 |
| 6,921,361 B2 * | 7/2005 | Suzuki | A61B 1/00098 600/104 |
| 8,128,592 B2 * | 3/2012 | Mitelberg | A61B 10/02 604/93.01 |
| 9,872,727 B2 * | 1/2018 | Motai | A61B 18/14 |
| 2004/0176751 A1 * | 9/2004 | Weitzner | A61B 17/0469 606/1 |
| 2005/0209612 A1 * | 9/2005 | Nakao | A61B 17/062 606/144 |
| 2005/0234294 A1 * | 10/2005 | Saadat | A61B 1/0008 600/104 |
| 2006/0064113 A1 * | 3/2006 | Nakao | A61B 10/06 606/113 |
| 2006/0100614 A1 * | 5/2006 | Long | A61B 18/14 606/27 |
| 2007/0282358 A1 * | 12/2007 | Remiszewski | A61B 17/00 606/159 |
| 2009/0018602 A1 | 1/2009 | Mitelberg et al. | |
| 2010/0185217 A1 * | 7/2010 | Hsu | A61B 1/00087 606/144 |
| 2011/0276038 A1 * | 11/2011 | McIntyre | A61B 17/00234 606/1 |
| 2012/0226287 A1 | 9/2012 | Qadeer | |

* cited by examiner

ENDOSCOPIC TISSUE MANIPULATION TOOL

CROSS-REFERENCE TO RELATED APPLICATIONS

This application claims the benefits of priority from U.S. Provisional Application No. 62/267,763, filed on Dec. 15, 2015, the disclosure of which is incorporated by reference herein in its entirety.

TECHNICAL FIELD

Aspects of the present disclosure generally relate to systems and methods of manipulating tissue within a body. In particular, the current disclosure relate to devices and procedures for performing endoscopic dissection of tissue.

BACKGROUND

The field of endoscopy has for many years focused on techniques to remove tissue (e.g., lesion, tumor, etc.) located in the digestive tract as part of a therapeutic or diagnostic procedure. Endoscopic submucosal dissection (ESD) is an endoscopic procedure used to remove gastrointestinal tumors/polyps that have not yet entered the muscle layer. In the gastrointestinal tract, the submucosa is the layer of dense irregular connective tissue or loose connective tissue that supports the mucosa (moist tissue that lines some organs and body cavities throughout the body), as well as joins the mucosa to the bulk of underlying smooth muscle (fibers running circularly within the layer of muscle). ESD procedure typically involves an injection of a material, e.g., saline, gel, etc., into the submucosa to elevate a lesion, dissecting the submucosa beneath the lesion, and removing the dissected lesion from the body.

A typical ESD procedure involves the use of multiple tools to perform specific tasks in the dissection process. For example, an endoscopic tool with a needle end effector may first be inserted into the body for the injection of a material into the submucosa. A snare with a wire loop may then be inserted into the body to dissect the lesion, and a cauterization tool may be used to cauterize the wound and stop any bleeding. A tissue grasper may then be used to retrieve the dissected lesion. The use of multiple tools may increase the complexity of the procedure and the risk of complications (e.g., inadvertent damage to healthy tissue, etc.). The systems and methods described herein may alleviate some of the above described deficiencies.

SUMMARY

Aspects of the present disclosure relate to, among other things, endoscopic tissue manipulation. These aspects may include one or more of the features described below.

In one aspect of the present disclosure, a medical device is disclosed. The device may be configured to manipulate tissue within a body of a subject. The device may comprise an elongate shaft having a proximal end and a distal end. The distal end may be configured to be inserted into the body. The device may also include end effectors coupled to the distal end of the elongate shaft. The end effectors may include a needle pivotably coupled to the shaft and configured to inject a fluid into the tissue, and an articulating arm pivotably coupled to the shaft. The end effectors may also include a cutting wire extending between the needle and the arm.

Embodiments of the disclosed medical device may include one or more of the features described below. The end effectors may further include a tissue grasper slidably coupled to the shaft. The tissue grasper may include a plurality of fingers configured to transform from a retracted configuration to an expanded configuration, wherein distal ends of the plurality of fingers may be positioned closer to the shaft in the retracted configuration than in the expanded configuration. At least a portion of the articulating arm may extend over the tissue grasper. The shaft of the device may include a nub configured to stop sliding of the grasper past the nub. The articulating arm may be configured to transform from a retracted configuration to an expanded configuration, wherein in the retracted configuration, a distal end of the arm is positioned closer to the shaft than in the expanded configuration. In the retracted configuration of the articulating arm, a longitudinal axis of the needle may extend along a longitudinal axis of the shaft, and in the expanded configuration of the articulating arm, the longitudinal axis of the needle may make an angle between about 45-135° from the longitudinal axis of the shaft. The device may further include a circumferential sleeve slidably positioned around the shaft. The sleeve may be configured to slide from a first position around the articulating arm to a second position away from the articulating arm. A proximal end of the articulating arm may be coupled to the shaft at a hinge. The needle may be coupled to the shaft at a pivot. The pivot may be positioned distal to the hinge. At least a portion of the articulating arm may extend over at least a portion of the needle. The cutting wire may be configured to be coupled to a source of electrical power. The cutting wire may be coupled between a distal end of the needle and a distal end of the articulating arm. The shaft may include an elbow joint. The cutting wire may be electrically insulated from the needle and the articulating arm. The device may include one or more fluid conduits configured to deliver a fluid from a proximal end of the device to the needle.

In another aspect of the present disclosure, a method of manipulating tissue within a body of a subject using a medical device is disclosed. The method may comprise inserting a needle of the device into the tissue within the body. The needle may be coupled to the device at a pivot. The method may include, after inserting the needle, extending an articulating arm of the device away from a shaft of the device to extend a cutting wire between the arm and the needle. The method may further include rotating the cutting wire to sever the tissue.

Embodiments of the disclosed method may include one or more of the following aspects. Extending the articulating arm may also rotate the needle about the pivot. The method may further comprise transforming a tissue grasper of the device from a retracted configuration to an expanded configuration.

In yet another aspect of the present disclosure, a medical device configured to manipulate tissue within a body of a subject is disclosed. The device may comprise an elongate shaft having a proximal end and a distal end. The distal end may be configured to be inserted into the body. The device may also include end effectors coupled to the distal end of the elongate shaft. The end effectors may include a needle coupled to the shaft at a pivot. The needle may be configured to inject a fluid into the tissue. The end effectors may also include an articulating arm pivotably coupled to the shaft at a hinge. The arm may be configured to transform from a retracted configuration in which a distal end of the arm is positioned closer to the shaft to an extended configuration in which the distal end of the shaft is positioned further away from the shaft. The end effectors may also include a cutting wire extending between the needle and the arm. The cutting wire being configured to cut the tissue. The end effectors may further include a tissue grasper slidably coupled to the shaft. The tissue grasper may be configured to transform from a retracted configuration to an extended configuration when the arm transforms from the retracted configuration to the extended configuration.

Embodiments of the disclosed device may include one or more of the following features. The needle may be configured to rotate about the pivot when the arm transforms from the retracted configuration to the extended configuration.

It may be understood that both the foregoing summary and the following detailed description are exemplary and explanatory only, neither being restrictive of the inventions claimed below.

BRIEF DESCRIPTION OF THE DRAWINGS

The accompanying drawings, which are incorporated in and constitute a part of this specification, illustrate exemplary embodiments that, together with the written description, serve to explain the principles of this disclosure.

DETAILED DESCRIPTION

The present disclosure is now described with reference to an exemplary endoscopic tissue dissecting medical device and an exemplary method of using the device. However, it should be noted that, reference to this particular device and procedure is provided only for convenience and not intended to limit the disclosure. A person of ordinary skill in the art would recognize that the concepts underlying the disclosed exemplary device and method may be utilized in any device or procedure, medical or otherwise. The discussion below uses the terms "proximal" and "distal" to refer to the relative positions of the device and its components. The term proximal refers to a position closer to a user using the device, and the term distal refers to a position further away from the user.

Figure 1:
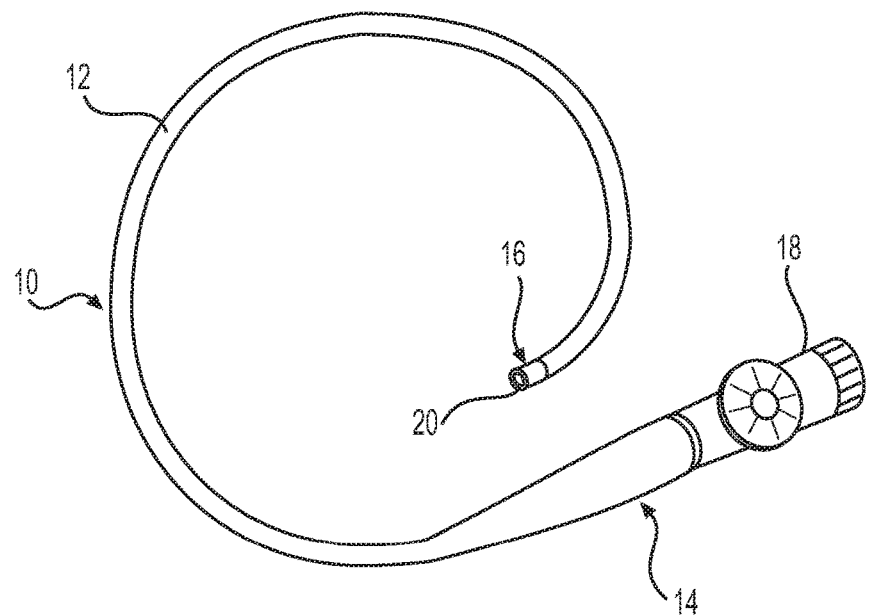
FIG. 1 illustrates an exemplary endoscope that may be used in the current disclosure.

FIG. 1 illustrates an endoscope 10 for use with an embodiment of the disclosed medical device. Endoscope 10 may include an elongate flexible tubular section 12 extending from a proximal end 14 to a distal end 16. Tubular section 12 may include any appropriate polyimide tube or a hollow member of another material that exhibits suitable flexibility, stiffness, and biocompatibility. In general, tubular section 12 may have any outer dimension (e.g., diameter) and cross-sectional shape configured for insertion into a body lumen directly or through a channel of an insertion device. The proximal end 14 of tubular section 12 may be coupled to a handle 18. One or more lumens may extend along the length of the tubular section 12 from the proximal end 14 to the distal end 16. The lumen may have an inner dimension and cross-sectional shape suitable for the insertion of one or more tools (medical devices) therethrough. Endoscope 10 may include other features that are found in endoscopes known in the art. Since endoscopes and their features are well known in the art, for the sake of brevity, these features are not discussed herein.

In use, the distal end 16 of the tubular section 12 may be inserted into the body of a patient through a natural orifice (mouth, rectum, etc.) and pushed in to position the distal end 16 proximate a desired worksite (e.g., a tissue lesion) within the body. After insertion, the proximal end 14 along with the handle 18 is positioned outside the body and the distal end 16 is positioned within the body. The handle 18 of the endoscope 10 may include knobs, actuators, and other control mechanisms that enable the tubular section 12 to be maneuvered (bent, flexed, etc.) from outside the body. The flexible nature of the tubular section 12 may enable the endoscope 10 to traverse tortuous body cavities without causing undue trauma to surrounding tissue. As is known in the art, the distal end 16 of the endoscope 10 may include lighting and imaging capability (camera, etc.) that enables a region in front of the distal end 16 to be viewed on a monitor positioned outside the body. The tubular section 12 may also include conduits for transporting utilities (electrical signals and power, fluids, aspiration, etc.) to and from the distal end 16. When the distal end 16 of the endoscope 10 is suitably positioned within the body, one or more medical devices (tools) may be inserted into the body through the lumen of the tubular section 12.

Figure 2:
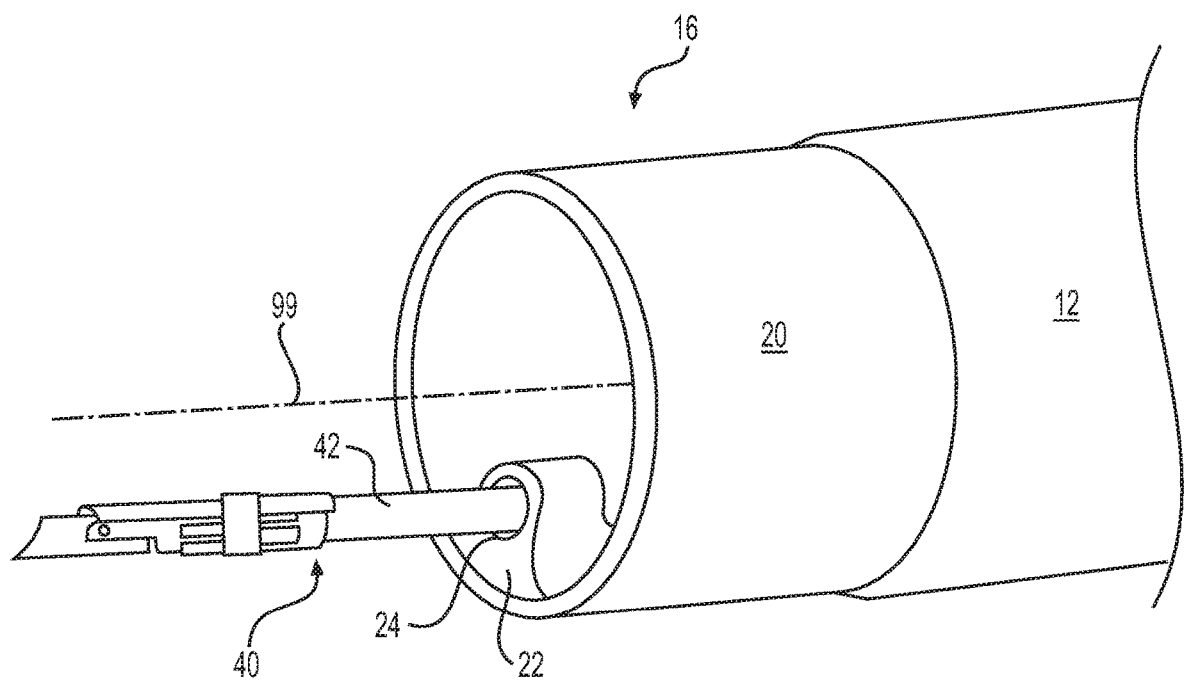
FIG. 2 is an exemplary medical device of the current disclosure extending into the body through the distal end of the endoscope of FIG. 1.

In some embodiments, a cap 20 may be attached to the distal end 16 of the tubular section 12 prior to insertion in to the body. FIG. 2 illustrates an enlarged view of the distal end 16 with an exemplary cap 20 attached thereto. Cap 20 may be a tubular sleeve-like member with a lumen extending along a longitudinal axis 99 of the cap 20. When the cap 20 is attached to the tubular section 12, the lumen of the cap 20 may be coaxial with the lumen of the tubular section 12. Cap 20 may include one or more structural features defined on its inner surface. These structural features may include a boss 22 that protrudes from the inner surface of the cap 20 and extends parallel to longitudinal axis 99. In general, boss 22 may include any shape and size. In some embodiments, as illustrated in FIG. 2, boss 22 may be a rounded protrusion that extends from the inner surface towards the longitudinal axis 99. Boss 22 may include a lumen 24 that extends parallel to the longitudinal axis 99. In some embodiments, a longitudinal axis (not shown) of the lumen 24 may be substantially parallel to longitudinal axis 99 of the cap 20. In this disclosure, relative terms, such as, "substantially," "about," etc. are used to indicate a possible variation of 10%.

The tools inserted though the lumen of the tubular section 12 may include a tool 40 that extends to the worksite within the body through lumen 24 of the boss 22. Tool 40 may include an elongate shaft 42 that extends through the lumen of the tubular section 12 of the endoscope 10 and the lumen 24 of the cap 20 into the body. In some embodiments, shaft 42 may be a flexible shaft that deflects or flexes to correspond to the curves in the tubular section 12. As will be described later, in some embodiments, shaft 42 may also include joints (elbow joints, union joints, etc.) that enable the shaft to bend at the joint. The distal end of the shaft 42 may include end effectors that assist in manipulating (grasping, cutting, piercing, etc.) tissue at the worksite. The proximal end (not shown) of the tool 40 may extend outside the body and include devices (e.g., actuators, controls, switches, etc.) adapted to manipulate (e.g., move, articulate, activate, etc.) the end effectors at the distal end.

Figure 3A:
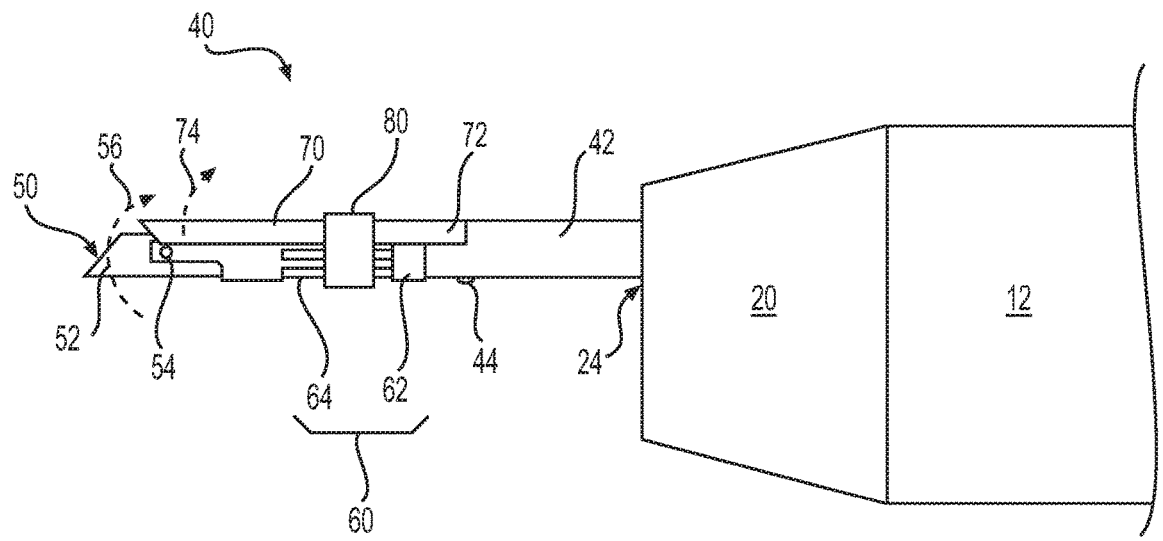
FIG. 3A is a side view of the medical device of FIG. 2 in its retracted configuration.
Figure 3B:
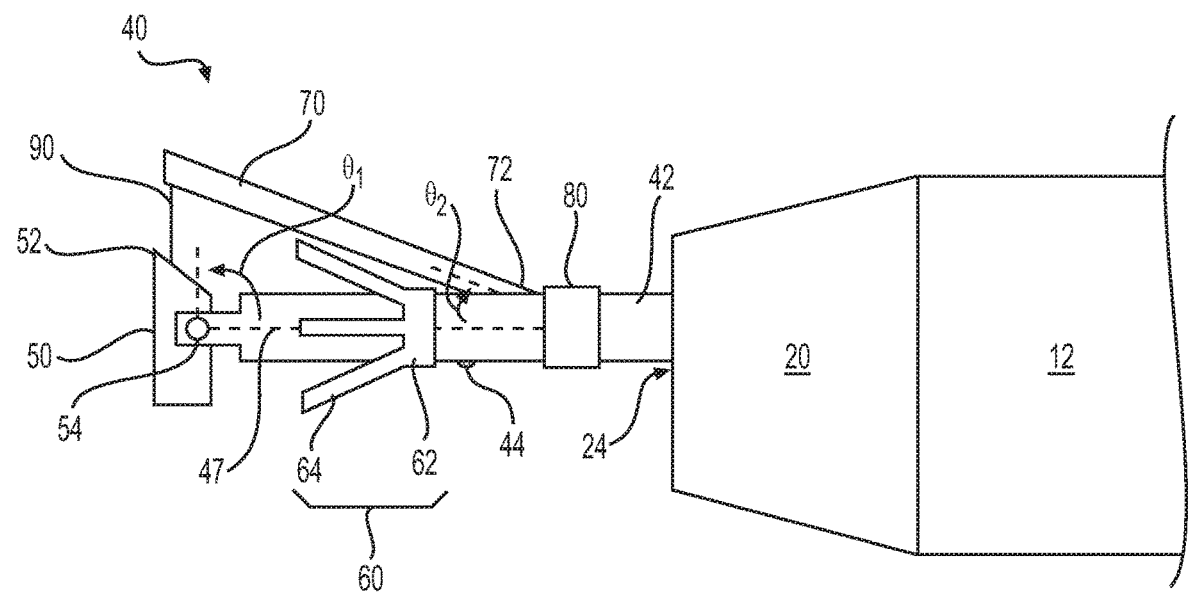
FIG. 3B is a side view of the medical device of FIG. 2 in its expanded configuration.

FIGS. 3A and 3B illustrate a side view of the cap 20 with the tool 40 extending into the body through its lumen 24. FIG. 3A illustrates the tool 40 with its end effectors in a retracted configuration, and FIG. 3B illustrates the tool 40 with its end effectors in an expanded configuration. The outer diameter of the tool 40 and the inner diameter of the lumen 24 may be such that the tool 40 may move freely (laterally and transversely) within the lumen 24. In some embodiments, to assist in insertion of the tool 40 into the lumen 24, the inner diameter of the lumen 24 may be greater than the outer diameter of the distal end of shaft 42 with its end effectors in a retracted configuration. In general, the end effectors may be configured to manipulate tissue within the body in any manner. In some embodiments, the end effectors may be configured to cooperatively cut or dissect tissue at the worksite and remove the dissected tissue from the body. Any number of end effectors may be provided at the distal end of shaft 42. In some embodiments, these end effectors may include a needle 50, an articulating arm 70, a cutting wire 90, and a tissue holder 60.

The needle 50 may be pivotably coupled to the distal most end of the shaft 42 at a pivot 54. The needle 50 may include a lumen and a sharp tip 52 at its distal end to pierce tissue at the worksite. The needle 50 may also be configured to inject a fluid (e.g., saline or another solution) through its lumen into the tissue. The tool 40 may include conduits configured to deliver the fluid from outside the body to the tip 52 of the needle 50 through the shaft 42 and the tubular section 12 of the endoscope 10. These conduits may comprise cavities that extend through the shaft 42 and flexible conduits (e.g., tubes) that extend across joints and other discontinuities (e.g., pivot 54) along its path. These cavities and the flexible conduits are not illustrated in FIGS. 3A and 3B for the sake of clarity. The needle 50 may have any size (e.g., gauge) and shape and may be made of any biocompatible material known in the art. In some embodiments, the needle 50 may be made of a metallic material. In some embodiments, a ceramic material may be used. As will be described later, upon the application of a force, the needle 50 may be configured to rotate about the pivot 54 (as illustrated by the dashed arrows 56 in FIG. 3A) from the configuration illustrated in FIG. 3A to the configuration illustrated in FIG. 3B. The needle 50 may be configured to rotate about the pivot 54 by any angle. In some embodiments, in the rotated configuration (of FIG. 3B), the needle 50 may make an angle $\theta_1$ of about 70-120° about a longitudinal axis 47 of the distal end of the shaft 42. In some embodiments, angle $\theta_1$ may be about 90°.

The distal end of the tool 40 may also include an end effector in the form of an articulating arm 70. The arm 70 may be hinged to the shaft 42 at a hinge 72. In some embodiments, the arm 70 may be a separate part attached to the shaft 42 at the hinge 72. In some embodiments, the arm 70 may be formed of a portion of the shaft 42 separated from the rest of the shaft 42 by a region of reduced thickness that forms a living hinge 72. Upon the application of a force, the arm 70 may be configured to rotate (as shown by dashed arrow 74 in FIG. 3A) about the hinge 72 from the retracted configuration illustrated in FIG. 3A to the expanded configuration illustrated in FIG. 3B. The opening force for the arm 70 may be applied by any known method. For example, in some embodiments, control wires (not shown) connecting the arm 70 to the proximal end of the tool 40 may be actuated by a user to transform the arm 70 to its expanded configuration. In some embodiments, the arm 70 may be a spring-loaded member which is biased in its expanded configuration (see FIG. 3B). A sleeve 80, that circumferentially fits around the shaft 42 and the arm 70, may constrain the arm 70 in its retracted configuration (see FIG. 3A). When the sleeve 80 is translated proximally past the hinge 72 (e.g., by sliding the sleeve 80 on the shaft 42 in a proximal direction), the constraining force on the arm 70 is released, and the arm 70 transforms to its expanded configuration by rotating about the hinge 72 (see FIG. 3B). When the sleeve 80 is translated distally, it forces the arm 70 back to its retracted configuration (FIG. 3A) as it slides over the folded arm 70. The sleeve 80 may be moved distally and proximally by any known method. In some embodiments, control wires (not shown) that extend from the sleeve 80 to the proximal end 14 may be used by the user to move the sleeve 80 in the proximal and distal directions.

The articulating arm 70 may rotate about the hinge 72 by any amount while transforming to its expanded configuration. In some embodiments, in its expanded configuration, the articulating arm 70 makes an angle $\theta_2$ of about 20-50° with the longitudinal axis 47 of the distal end of the shaft 42. In some embodiments, the amount of rotation of the arm 70 may be controlled by the user. For example, in some embodiments, the sleeve 80 may be positioned partially over the hinge 72 to limit the rotation of the arm 70. In some embodiments, a control wire may be actuated to achieve a desired rotation of the arm 70.

The distal end of the tool 40 may also include an end effector in the form of a cutting wire 90. The cutting wire 90 may be connected between the distal ends of the articulating arm 70 and needle 50 (i.e., the needle tip 52). When the arm 70 transforms from its retracted to its expanded configuration, the lateral (or pulling) force applied by the cutting wire 90 on the needle tip 52 rotates the needle 50 about the pivot 54 (as illustrated by dashed arrow 56 in FIG. 3A) from the configuration illustrated in FIG. 3A to the configuration illustrated in FIG. 3B. The cutting wire 90 may be provided with sufficient slack so that when the arm 70 transforms to its expanded configuration, the cutting wire 90 is held taut between the distal end of the arm 70 and the needle tip 52. In some embodiments, one end of the cutting wire 90 may extend to the proximal end through the shaft 42, and the length of the cutting wire 90 may be controlled by the user to control the rotation or lift (i.e., the amount by which the arm 70 lifts off the shaft 42) of the arm 70 in the expanded configuration. The cutting wire 90 may be made of any biocompatible material (metallic, polymeric, etc.) that is adapted to cut through tissue when it is pressed against the tissue.

In some embodiments, the cutting wire 90 may be configured to cut the tissue using electrosurgical techniques. For instance, the cutting wire 90 may be configured to apply high frequency electric current to the tissue as a means to cut, coagulate, desiccate, or fulgurate tissue. In some embodiments, cutting wire 90 may be configured to be electrically heated (e.g., by joule heating) for cauterization of tissue. In some embodiments, the cutting wire 90 may be electrically connected to a power supply (AC or DC) positioned outside the body, and may be electrically insulated from the arm 70 and the needle 50. In some embodiments some or all portions of the arm 70 and/or the needle 50 may be made of an electrically insulating material (e.g., ceramic, etc.) to electrically isolate the cutting wire 90 from other components of the tool 40. In some embodiments, the tool 40 may be configured to deliver a fluid (gas, liquid, etc.) to the tissue to aid (e.g., cool, etc.) in the tissue cutting process.

The distal end of the shaft 42 may also include the tissue holder 60. As illustrated in FIG. 3B, the tissue holder 60 may include a plurality of fingers 64 extending distally from a collar 62. The fingers 64 may be configured to transform from a retracted configuration (see FIG. 3A) to an expanded configuration (see FIG. 3B). In general, any known method (control wires, etc.) may be used to transform the fingers 64 between their retracted and expanded configurations. In some embodiments, similar to the functioning of the spring-loaded articulating arm 70 described above, the fingers 64 may be spring-loaded elongate members that are configured to transform from their retracted configuration to their expanded configuration upon the release of a constraining force. The articulating arm 70 and/or the sleeve 80 may provide the constraining force to keep the fingers 64 in their retracted configuration. Sliding the sleeve 80 off the arm 70 and/or the tissue holder 60 may release the constraining force from the fingers 64 and allow them to transform to the expanded configuration. Sliding the sleeve 80 over the fingers 64 may transform the fingers 64 back to the retracted configuration. The collar 62 may be a tubular sleeve-like member that extends circumferentially over the shaft 42. In some embodiments, the inner diameter of the collar 62 and the outer diameter of the shaft 42 may be such that the collar 62 may slide freely over, and rotate independently around, the shaft 42. In some embodiments, the shaft 42 may include a nub 44 (or another feature, such as, a notch, groove, protrusion, etc.) proximal and/or distal to the collar 62 to serve as a stop for the collar 62. The nub 44 may limit the translation of the collar 62 on the shaft 42 by preventing the collar 62 from sliding past it. The tissue holder 60 may be made of any resilient biocompatible material (e.g., nitinol, stainless steel, etc.).

Figure 4:
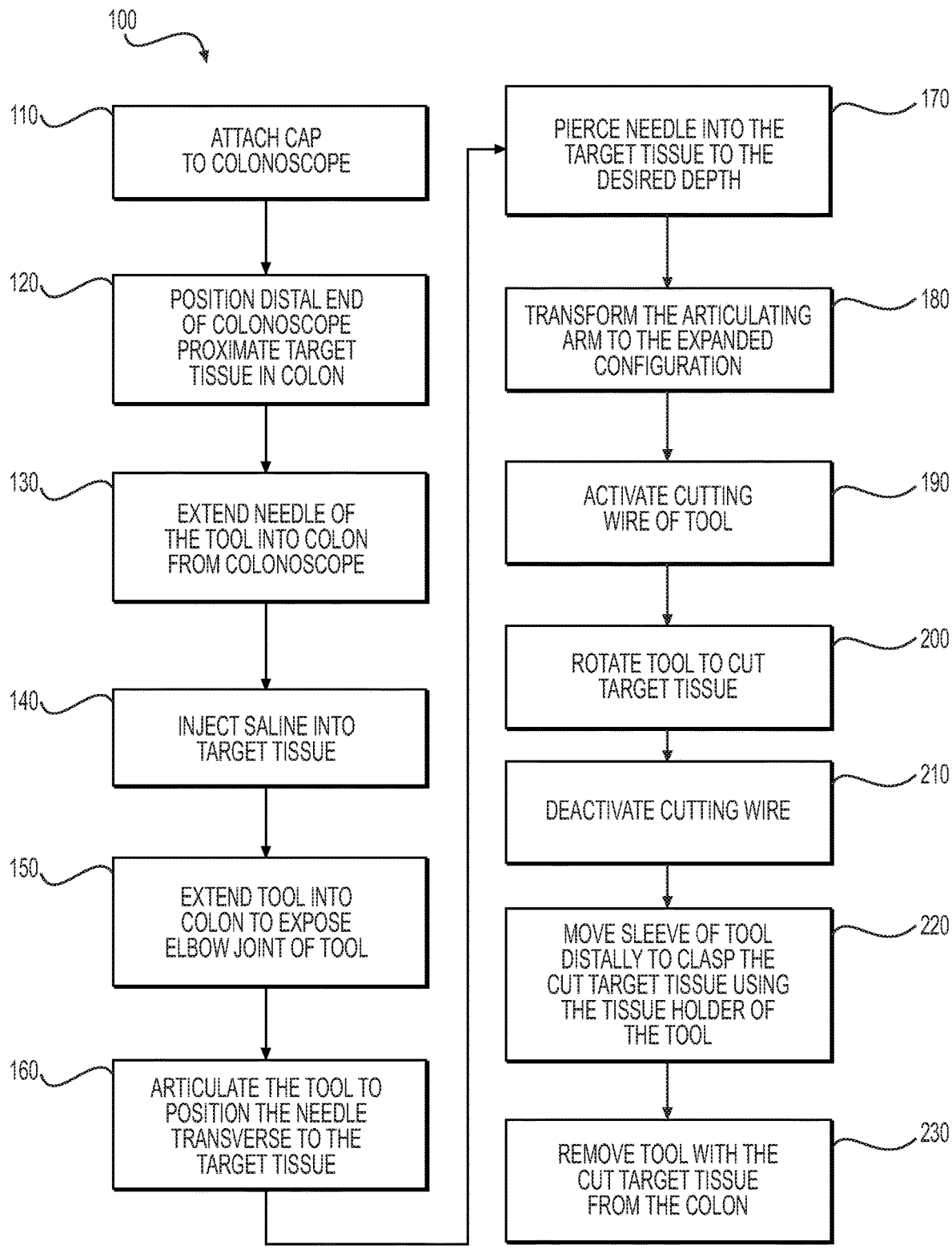
FIG. 4 is a flow chart of an exemplary method of using the medical device of FIG. 2.
Figure 5:
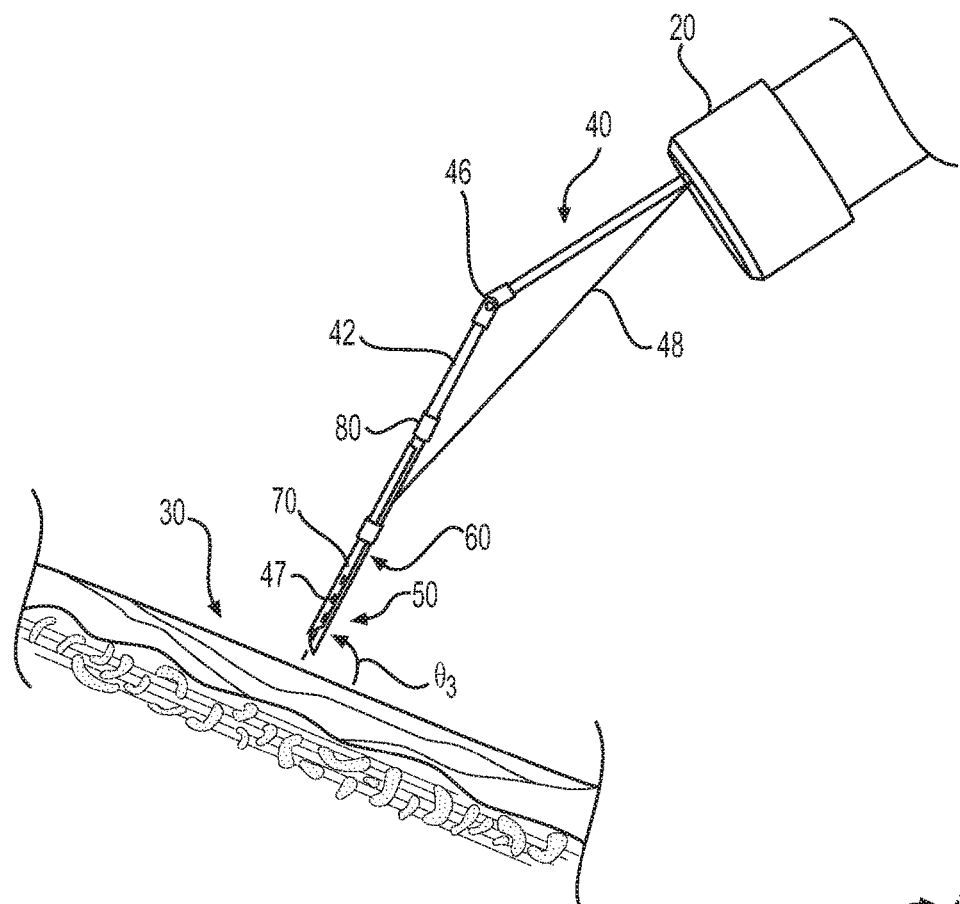
FIG. 5 illustrates the medical device of FIG. 2 prior to being inserted into tissue in the colon of a patient.
Figure 6:
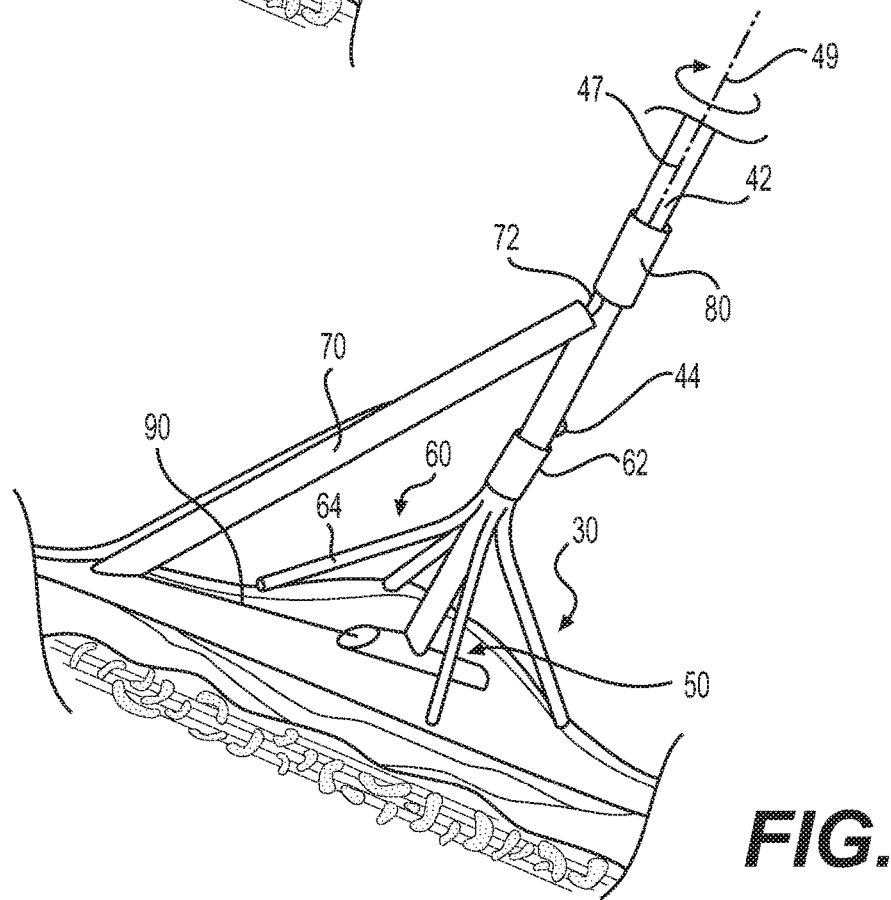
FIG. 6 illustrates the medical device of FIG. 2 prior to dissecting the tissue.

An exemplary method 100 of manipulating tissue using the exemplary tool 40 will now be described with reference to FIGS. 4-6. FIG. 4 is a flow chart illustrating the steps in the exemplary method 100, and FIGS. 5 and 6 are illustrations of the tool 40 while performing some of the steps in method 100 of FIG. 4. In the discussion, reference will be made to FIGS. 4-6. In the discussion that follows, an exemplary method 100 of using the tool 40 to perform en-block dissection (removal of a large bulky tumor or lesion as a single part) of target tissue 30 in the colon wall is discussed. However, it should be noted that this procedure is only exemplary, and the tool 40 may be used for any suitable procedure. In 110, the cap 20 is attached to the distal end of a colonoscope (a type of endoscope) (110). Alternatively, in some embodiments, the colonoscope may already include the cap 20. The distal end of the colonoscope with the cap 20 is then inserted into the colon through the rectum of a patient and suitably positioned proximate the target tissue 30 on the colon wall (120). An imaging device at the distal end of the colonoscope may assist in maneuvering the colonoscope to the target tissue 30. The tool 40 may then be inserted into colonoscope with the needle 50 extending through the lumen 24 of the cap 20 (see FIG. 2). In some embodiments, the colonoscope along with the tool 40 pre-inserted thereinto may be inserted into the colon in 120. The needle 50 of the tool 40 may then be extended out of the distal end of the colonoscope (130).

The tip 52 of the needle may be used to pierce the target tissue 30 and inject saline solution (or another suitable submucosal injection solution) into the tissue to lift the target tissue 30 from the underlying muscle (140). The tool 40 may then be extended further out of the distal end of the colonoscope as illustrated in FIG. 5. After extending, the tool 40 may be positioned such that an articulating joint 46 (e.g., an elbow joint) on the shaft 42 is located outside the colonoscope (150). A control wire 48 connected to the shaft 42 distal of joint 46 may then be actuated (e.g., pulled from outside the body) to bend the shaft 42 at the joint 46, and orient the distal end of the shaft 42 transverse to the target tissue 30 (160). It should be noted that bending the shaft 42 at the joint 46 using a control wire 48 is only exemplary. In general, the shaft 42 may be bent in any known manner (e.g., flexible articulating shaft, etc.) and by any amount. In some embodiments, the shaft 42 may be bent such that the longitudinal axis 47 of the distal end of the shaft 42 makes an angle $\theta_3$ of about 45-135° with the tissue surface.

The needle 50 may be pierced into the target tissue to the desired depth (170). In some embodiments, the needle 50 and/or the distal end of the shaft 42 may include markers to indicate the depth of penetration. In some embodiments, the depth by which the needle 50 is pierced into the target tissue 30 (i.e., 170) may correspond to the depth of the tissue to be removed. Piercing the needle 50 into the target tissue also causes the distal end of the arm 70 to penetrate the target tissue 30 since the distal-most end of arm 70 is just proximal of needle tip 52. The articulating arm 70 may then be transformed to its expanded configuration (180). In embodiments of the tool 40 with the circumferential sleeve 80 positioned around a spring-loaded arm 70, the sleeve 80 may be translated in a proximal direction past the hinge 72 to transform the arm 70 to its extended configuration. FIG. 6 is an illustration of the tool 40 with its needle 50 positioned within in the target tissue 30 and its arm 70 in the extended configuration. Since piercing the needle 50 into the target tissue (i.e., 170) causes the distal end of the arm 70 to enter the tissue, lifting the arm 70 to its expanded configuration causes some of the tissue adjacent to the arm 70 to tear or otherwise separate from underlying tissue. In some embodiments, as illustrated in FIG. 6, the depth of penetration of the needle 50 in 170 (and/or the distance between the distal-most end of arm 70 and the needle tip 52) may be selected such that the distal end of the arm 70 is positioned external to the tissue when the arm is transformed to its expanded configuration.

As explained previously, transforming the arm 70 to its expanded configuration (180) causes the needle 50 to rotate about the pivot 54 (see FIGS. 3A and 3B) and the cutting wire 90 to stretch from the needle tip 52 to the distal end of the arm 70. Transforming the arm 70 to its expanded configuration (180) by moving the sleeve 80 proximally also the releases the constraining force on the tissue holder 60 and causes its fingers 64 to transform to its expanded configuration. In some embodiments, in 170, the needle 50 is pierced into the target tissue until the tips of the fingers 64 are positioned just above the tissue surface so that, in the expanded configuration, the tips of the expanded fingers 64 are located just above the target tissue surface. In some embodiments, in the expanded configuration, the distal tips of the fingers 64 may press against the target tissue surface. In some embodiments, the tool 40 may be pushed inwards (i.e., forced/moved in the distal direction) after the tissue holder 60 is released to press the distal tips of the fingers 64 against the target tissue. As the tool 40 is pushed inwards, the nub 44 (see FIG. 3B) on the shaft 42 may interact with the collar 62 and cause the tips of the fingers 64 to press against the target tissue.

The cutting wire 90 may then be activated (190). Activating the cutting wire 90 may include activating the electric power supply to the cutting wire 90 (for heating the cutting wire). In some embodiments, the cutting wire 90 may be activated before the arm 70 is transformed to the expanded configuration (i.e., 180). The shaft 42 of the tool 40 may be rotated (see arrow 49 in FIG. 6) about its longitudinal axis 47 like a compass to cut the target tissue 30 using the cutting wire 90 (200). The shaft 42 may be rotated by any known method. In some embodiments, the proximal end of the shaft 42 positioned outside the body may be rotated to rotate the distal end of the shaft 42. Rotating the shaft 42 rotates the expanded arm 70 along with it, and causes the cutting wire 90 to sweep through and sever the tissue through which the cutting wire 90 traverses. In some embodiments, the shaft 42 may be rotated by about 360° around its longitudinal axis 47 to circumferentially cut under the target tissue 30 and completely separate the target tissue 30 from the colon wall. As the heated cutting wire 90 cuts through the tissue, the heat of the wire causes the wound to be cauterized and stop bleeding.

As the shaft 42 rotates about its longitudinal axis 47, the circumferential collar 62 of the tissue holder 60 allows the shaft 42 to rotate without causing the tissue holder 60 to rotate along with the shaft 42. As the shaft 42 rotates relative to the tissue holder 60, the tips of the fingers 64 pressing against the target tissue surface may provide traction for the tool 40 during the cutting operation. After cutting the target tissue, the cutting wire 90 may be deactivated (210). Deactivating the cutting wire may include shutting off the electric power to the cutting wire 90. The sleeve 80 may then be moved distally over the arm 70 and the fingers 64 of the tissue holder 60 (220). As the sleeve 80 slides over the arm 70 and the fingers 64, the arm 70 and the fingers 64 are forced inwards (towards shaft 42) to their retracted configurations. As the fingers 64 move to their retracted configuration, the collapsing fingers 64 grasp the freshly cut target tissue 30. The tool 40 with the cut target tissue 30 is then removed from the colon (230). In some embodiments, the tool 40 may be retracted into the colonoscope, and the colonoscope removed from the body. In some embodiments, the tool 40 with the dissected target tissue is removed from the body through the colonoscope leaving the colonoscope in place for further procedures.

Using the endoscopic submucosal dissection method described above, a large volume of target tissue may be separated and removed from the colon wall as a single piece without having to dissect the tissue into multiple pieces. The volume of target tissue removed may be controlled by controlling the depth of penetration of the needle 50 into the tissue (170) and the lift of the arm 70 in its expanded configuration. Performing this procedure using a single tool which includes the end effectors to perform the entire procedure simplifies the procedure and reduces the possibilities of medical complications.

Other examples of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

The invention claimed is:

1. A medical device configured to manipulate tissue within a body of a subject, comprising:
    an elongate shaft having a proximal end and a distal end, the distal end configured to be inserted into the body;
    end effectors coupled to the distal end of the elongate shaft, wherein the end effectors include (a) a needle pivotably coupled to the shaft and configured to inject a fluid into the tissue, (b) an articulating arm pivotably coupled to the shaft, and (c) a cutting wire extending between the needle and the arm; and
    a circumferential sleeve slidably positioned around the shaft, and wherein the sleeve is configured to slide from a first position around the articulating arm to a second position away from the articulating arm.

2. The device of claim 1, wherein the end effectors further include a tissue grasper slidably coupled to the shaft.

3. The device of claim 2, wherein the tissue grasper includes a plurality of fingers configured to transform from a retracted configuration to an expanded configuration, wherein distal ends of the plurality of fingers are positioned closer to the shaft in the retracted configuration than in the expanded configuration.

4. The device of claim 2, wherein at least a portion of the articulating arm extends over the tissue grasper.

5. The device of claim 2, wherein the shaft includes a nub configured to stop sliding of the gasper past the nub.

6. The device of claim 1, wherein the articulating arm is configured to transform from a retracted configuration to an expanded configuration, wherein in the retracted configuration, a distal end of the arm is positioned closer to the shaft than in the expanded configuration.

7. The device of claim 6, wherein in the retracted configuration of the articulating arm, a longitudinal axis of the needle extends along a longitudinal axis of the shaft, and in the expanded configuration of the articulating arm, the longitudinal axis of the needle makes an angle between about 45-135° from the longitudinal axis of the shaft.

8. The device of claim 1, wherein a proximal end of the articulating arm is coupled to the shaft at a hinge, and the needle is coupled to the shaft at a pivot, wherein the pivot is positioned distal to the hinge.

9. The device of claim 1, wherein at least a portion of the articulating arm extends over at least a portion of the needle.

10. The device of claim 1, wherein the cutting wire is configured to be coupled to a source of electrical power.

11. The device of claim 1, wherein the cutting wire is coupled between a distal end of the needle and a distal end of the articulating arm.

12. The device of claim 1, wherein the shaft includes an elbow joint.

13. The device of claim 1, wherein the cutting wire is electrically insulated from the needle and the articulating arm.

14. The device of claim 1, further including one or more fluid conduits configured to deliver a fluid from a proximal end of the device to the needle.

15. A method of manipulating tissue within a body of a subject using a medical device, the method comprising:
    inserting a needle of the device into the tissue within the body, wherein the needle is coupled to the device at a pivot;
    after inserting the needle, extending an articulating arm of the device away from a shaft of the device to extend a cutting wire between the arm and the needle; and
    rotating the cutting wire to sever the tissue.

16. The method of claim 15, wherein extending the articulating arm also rotates the needle about the pivot.

17. The method of claim 15, further comprising transforming a tissue grasper of the device from a retracted configuration to an expanded configuration.

18. A medical device configured to manipulate tissue within a body of a subject, comprising:
    an elongate shaft having a proximal end and a distal end, the distal end configured to be inserted into the body; and end effectors coupled to the distal end of the elongate shaft, wherein the end effectors include (a) a needle pivotably coupled to the shaft and configured to inject a fluid into the tissue, (b) an articulating arm pivotably coupled to the shaft, and (c) a cutting wire extending between the needle and the arm, wherein the end effectors further include a tissue grasper slidably coupled to the shaft, and wherein the tissue grasper includes a plurality of fingers configured to transform from a retracted configuration to an expanded configuration, wherein distal ends of the plurality of fingers are positioned closer to the shaft in the retracted configuration than in the expanded configuration.

19. The device of claim 18, wherein the shaft includes a nub configured to stop sliding of the gasper past the nub.

20. The device of claim 18, wherein the articulating arm is configured to transform from a retracted configuration to an expanded configuration, wherein in the retracted configuration, a distal end of the arm is positioned closer to the shaft than in the expanded configuration.

* * * * *